United States Patent [19]

VandenBerg

[11] Patent Number: Plant 6,943

[45] Date of Patent: Jul. 25, 1989

[54] CHRYSANTHEMUM PLANT NAMED YELLOW VERO

[75] Inventor: Cornelis P. VandenBerg, Salinas, Calif.

[73] Assignee: Yoder Brothers, Inc., Barberton, Ohio

[21] Appl. No.: 173,722

[22] Filed: Mar. 25, 1988

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Yellow Vero particularly characterized by its flat capitulum form; daisy capitulum type; yellow ray floret color; diameter across face of capitulum of up to 85 mm at maturity; uniform nine week photoperiodic flowering response to short days; medium plant height when grown as a single stem spray cut mum; and excellent tolerance to low temperature for bud initiation and flower development.

3 Drawing Sheets

The present invention comprises a new and distinct cultivar of Chrysanthemum, botanically known as *Dendranthema grandiflora,* and referred to by the cultivar name Yellow Vero.

Yellow Vero, identified as 81064A02, is a product of a mutation induction program which had the objective of creating new Chrysanthemum cultivars that would expand the color range of an existing cultivar while retaining all other traits.

Yellow Vero was discovered and selected by Cornelis P. VandenBerg on Dec. 18, 1985 in a controlled environment in Salinas, Calif. as one flowering plant within a flowering block established as rooted cuttings from stock plants which had been exposed as unrooted cuttings to an X-ray source of 1750 rads. The irradiated parent was the cultivar identified as Vero, disclosed in U.S. Plant Pat. application Ser. No. 005,762.

The first act of asexual reproduction of Yellow Vero was accomplished when vegetative cuttings were taken from the initial selection in March 1986 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Yellow Vero are firmly fixed and are retained through successive generations of asexual reproduction.

Yellow Vero has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Yellow Vero, which, in combination, distinguish this Chrysanthemum as a new and distinct cultivar:

1. Flat capitulum form.
2. Daisy capitulum type.
3. Yellow ray floret color.

4. Diameter across face of capitulum up to 85 mm at maturity.
5. Uniform nine week photoperiodic flowering response to short days.
6. Peduncle length ranging from 15 to 20 cm on open terminal sprays.
7. Medium plant height requiring two long day weeks prior to short days to attain a flowered plant height of 100 to 110 cm for year-round flowerings.
8. Excellent tolerance to low temperatures for bud initiation and flower development.

The accompanying photographic drawings show typical inflorescence and leaf characteristics of Yellow Vero, with the colors being as nearly true as possible with illustrations of this type.

Sheet 1 is a color photograph of Yellow Vero grown as a single stem cut spray mum. It should be noted that despite repeated efforts, the bright yellow ray floret color indicated below was not able to be photographically depicted.

Sheet 2 is a black and white photograph of three views of the inflorescence of Yellow Vero.

Sheet 3 is a black and white photograph showing the upper and under sides of the leaves of Yellow Vero at three stages of development (mature, intermediate and immature).

Of the commercial cultivars known to the inventor, the most similar in comparison to Yellow Vero is the parent cultivar Vero. All traits of Yellow Vero are similar to those of Vero, except the color of ray florets. The color of the ray florets of Yellow Vero is a bright yellow, whereas Vero has white ray florets.

In the following description, color references are made to The Royal Horticultural Society Colour Chart. The color values were determined on plant material grown as a single stem cut spray mum in Salinas, Calif. on Oct. 17, 1987.

Classification:

*Botanical.*—*Dendranthema grandiflora,* cv Yellow Vero.

*Commercial.*—Daisy cut spray mum.

INFLORESCENCE

A. Capitulum: Form: Flat. Type: Daisy. Diameter across face: Up to 85 mm at maturity.

B. Corolla of ray florets:

*Color* (*general tonality from a distance of three meters*).—Yellow.

*Color* (*upper surface*).—5B when just opening; 4B when flower is completely open.

*Color* (*under surface*).—4C.

*Shape.*—Flat, oblong.

C. Corolla of disc florets:

*Color* (*mature*).—Closest to 12A to 12B.

*Color* (*immature*).—Closest to 144A to 144B.

D. Reproductive organs:

*Androecium.*—Present on disc florets only; scant pollen.

*Gynoecium.*—Present on both ray and disc florets.

PLANT

A. General appearance:

*Height.*—Medium; 100 to 110 cm as a single stem cut mum with two long day weeks prior to short days.

B. Foliage:

*Color* (*upper surface*).—137A.

*Color* (*under surface*).—137B.

*Shape.*—Lobed and slightly serrated.

I claim:

1. A new and distinct Chrysanthemum plant named Yellow Vero, as described and illustrated.

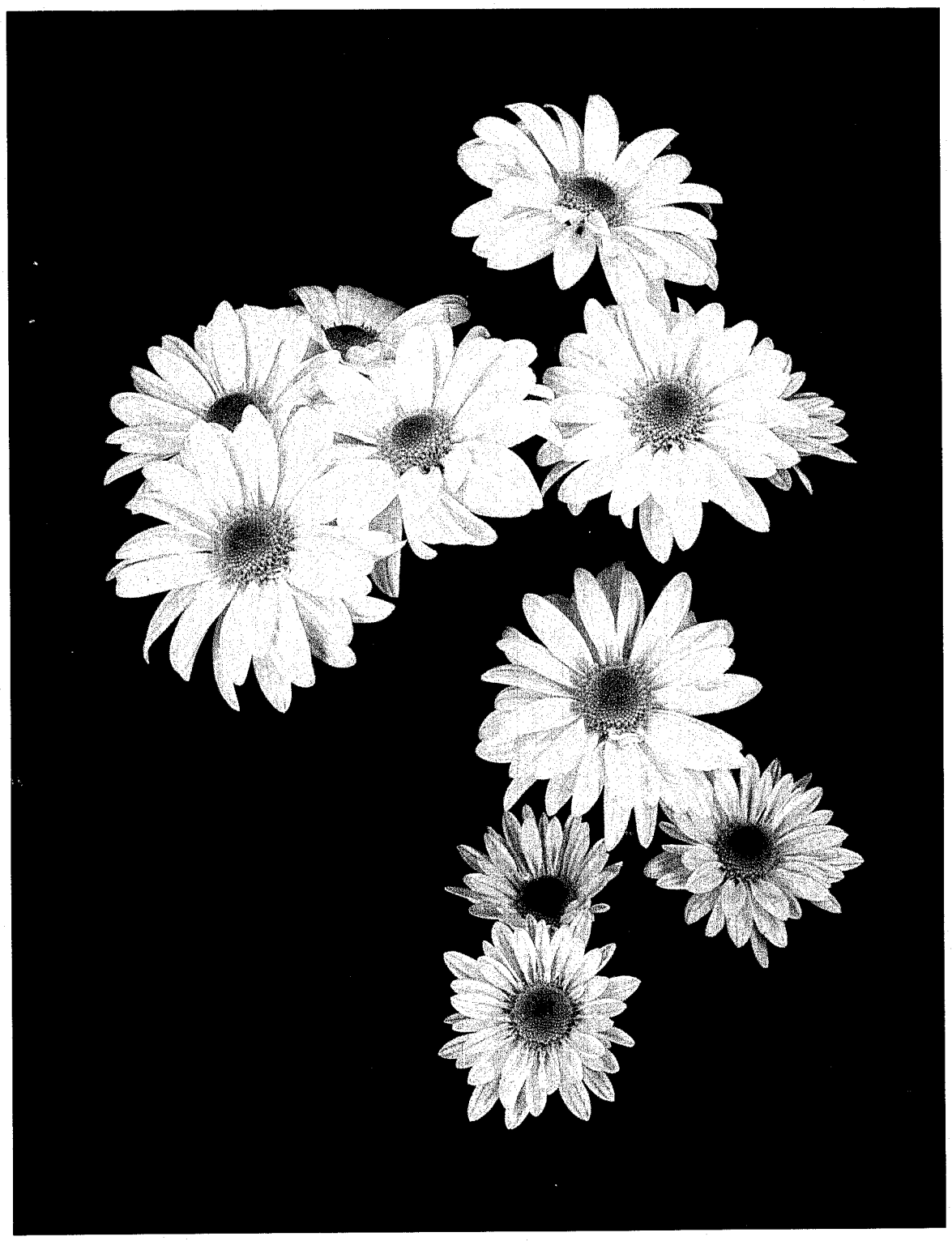

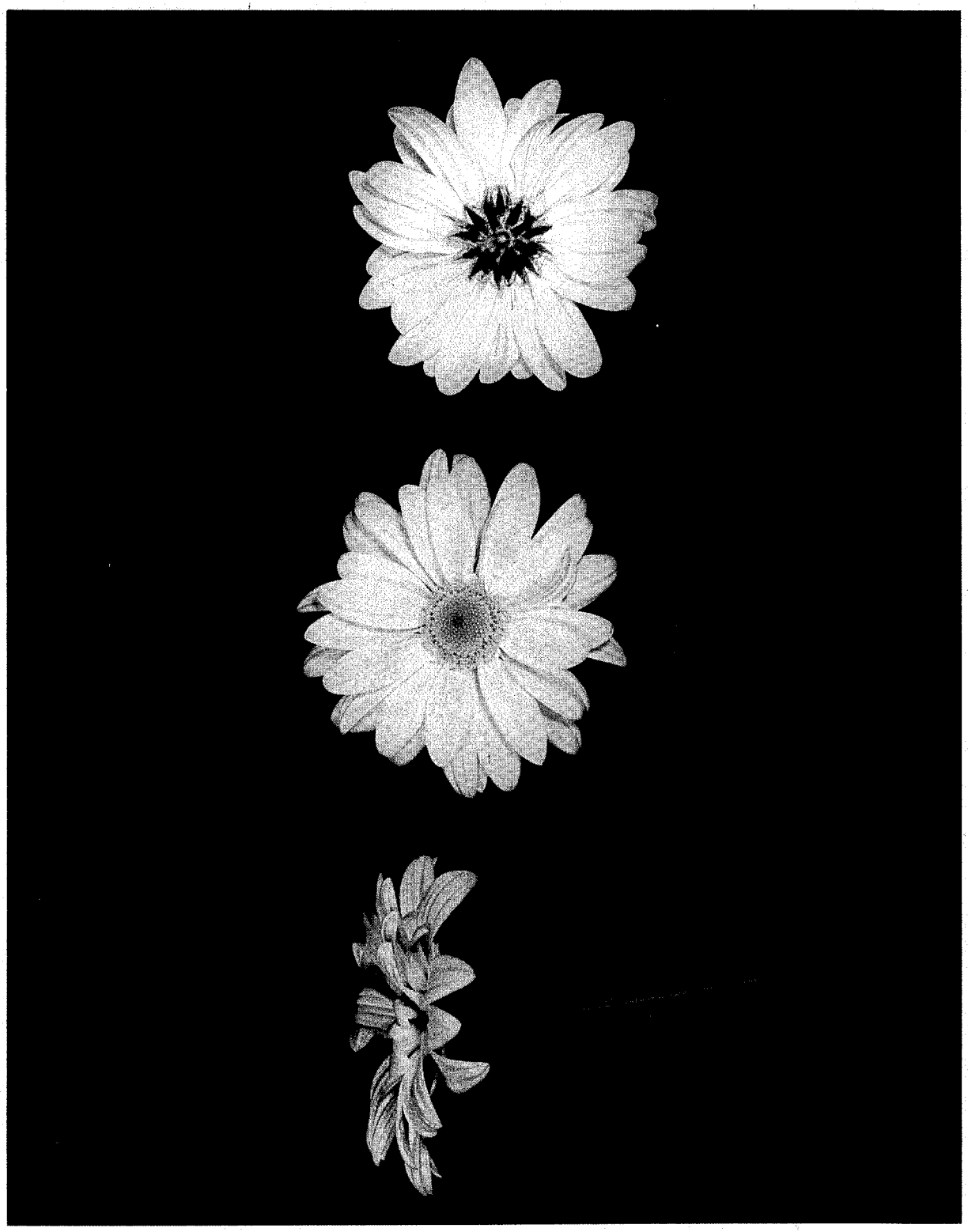

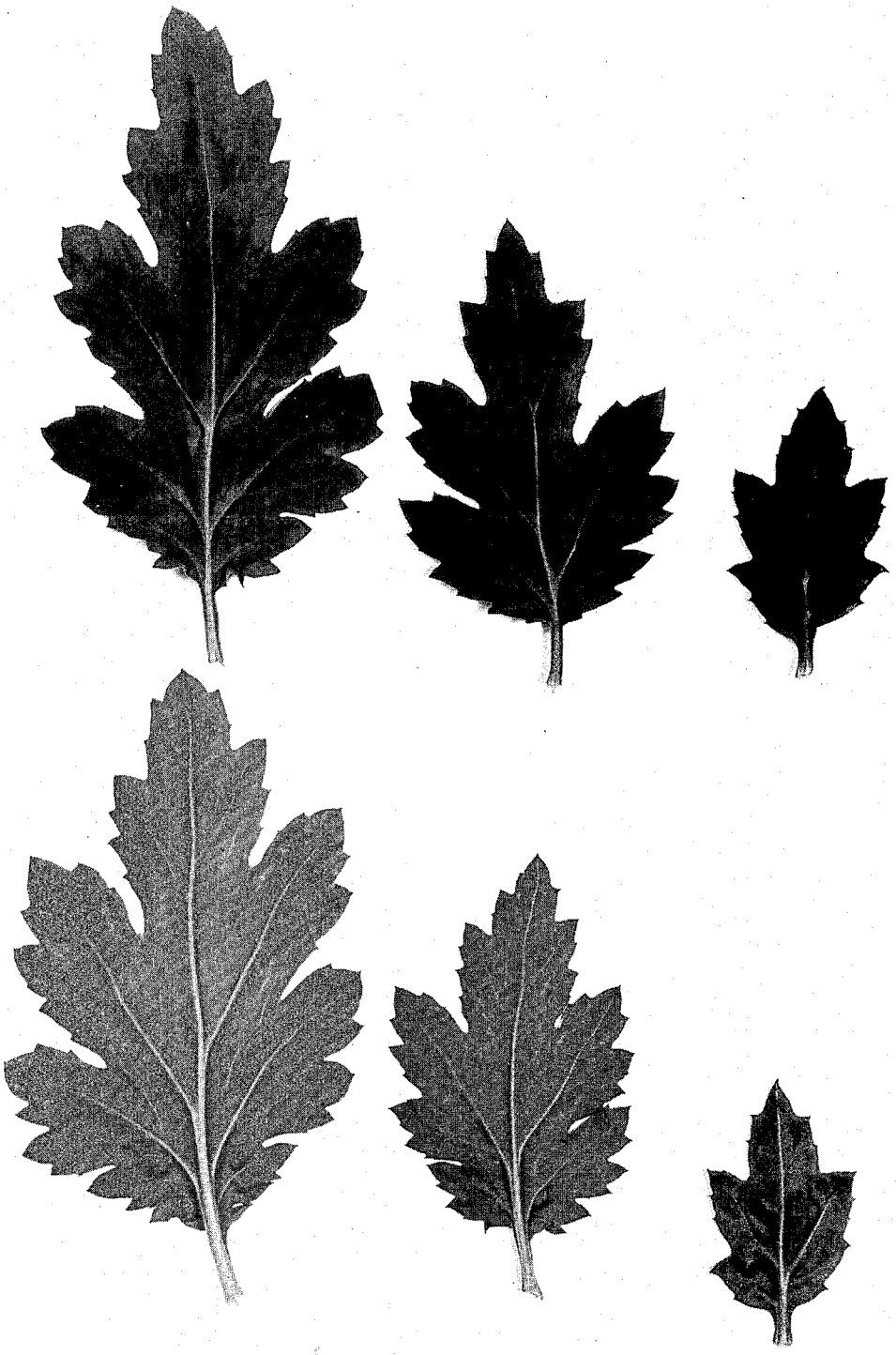

* * * * *